United States Patent [19]
Yabuta et al.

[11] Patent Number: 5,622,840
[45] Date of Patent: Apr. 22, 1997

[54] METHOD FOR CONTROLLING GENE EXPRESSION

[75] Inventors: Masayuki Yabuta, Tatebayashi; Seiko Miura, Konosu; Kazuhiro Ohsuye, Ohra-gun, all of Japan

[73] Assignee: Suntory Limited, Osaka, Japan

[21] Appl. No.: 456,923

[22] Filed: Jun. 1, 1995

[30] Foreign Application Priority Data

Jun. 1, 1994 [JP] Japan .................................. 6-140736
Aug. 3, 1994 [JP] Japan .................................. 6-200311

[51] Int. Cl.$^6$ ...................... C12P 21/02; C07K 14/245; C12N 15/31
[52] U.S. Cl. ................. 435/69.1; 435/320.1; 530/350; 536/23.7
[58] Field of Search ................... 530/350, 69.1; 435/252.3, 252.33, 240.2, 240.4, 320.1; 536/23.5, 23.7

[56] References Cited

PUBLICATIONS

Ulrich Deuschle et al., Proc. Natl. Acad. Sci., vol. 86, pp. 5400–5405, 1989.
Mickey C.T. Hu et al., Mol.Cell. Biol., vol. 10, pp. 6141–6151, 1990.
J.H. Miller, A Short Course in Bacterial Genetics, Laboratory Manual, pp. 131–134, Cold Spring Harbor Laboratory, 1992.
Huynh T.V. et al, DNA Cloning, vol. 1, IRL Press Limit. Oxford, England pp. 49–78 (1985).
Experiments in Molecular Genetics, pp. 352–355, Cold Spring Harbor Laboratory, 1972.

*Primary Examiner*—James Ketter
*Attorney, Agent, or Firm*—Burns, Doane, Swecker & Mathis

[57] ABSTRACT

A lactose repressor protein wherein at least one amino acid at the position of 94, 241, 265 or 300 in the wild lactose repressor is replaced with an amino acid other than that of the wild lactose repressor, and the use thereof.

The present mutant lactose repressor represses the expression of a desired gene at 30° C. or lower temperature, and induces the expression of a desired gene at 37° C. or higher temperature, and therefor can control the expression by change of a culture temperature without using an expensive inducer such as IPTG.

22 Claims, 5 Drawing Sheets

MYW3110/pMC9-1 (□)
MYW3110/pMC9-2 (○)
MYW3110/pMC9-16 (■)

1. MYW3110/pG97S4DhCT[GRRR], pYO16, 37°C
2. MYW3110/pG97S4DhCT[GRRR], pYO16, 30°C
3. MYW3110/pG97S4DhCT[GRRR], pYO1, 37°C
4. MYW3110/pG97S4DhCT[GRRR], pYO1, 30°C
5. MYW3110/pG97S4DhCT[GRRR], pYO2, 37°C
6. MYW3110/pG97S4DhCT[GRRR], pYO2, 30°C
7. MYW3110/pG97S4DhCT[GRRR], pYOW, IPTG ADDITION, 37°C
8. MYW3110/pG97S4DhCT[GRRR], pYOW, IPTG ADDITION, 30°C
9. MYW3110/pG97S4DhCT[GRRR], pYOW, 37°C
10. MYW3110/pG97S4DhCT[GRRR], pYOW, 30°C

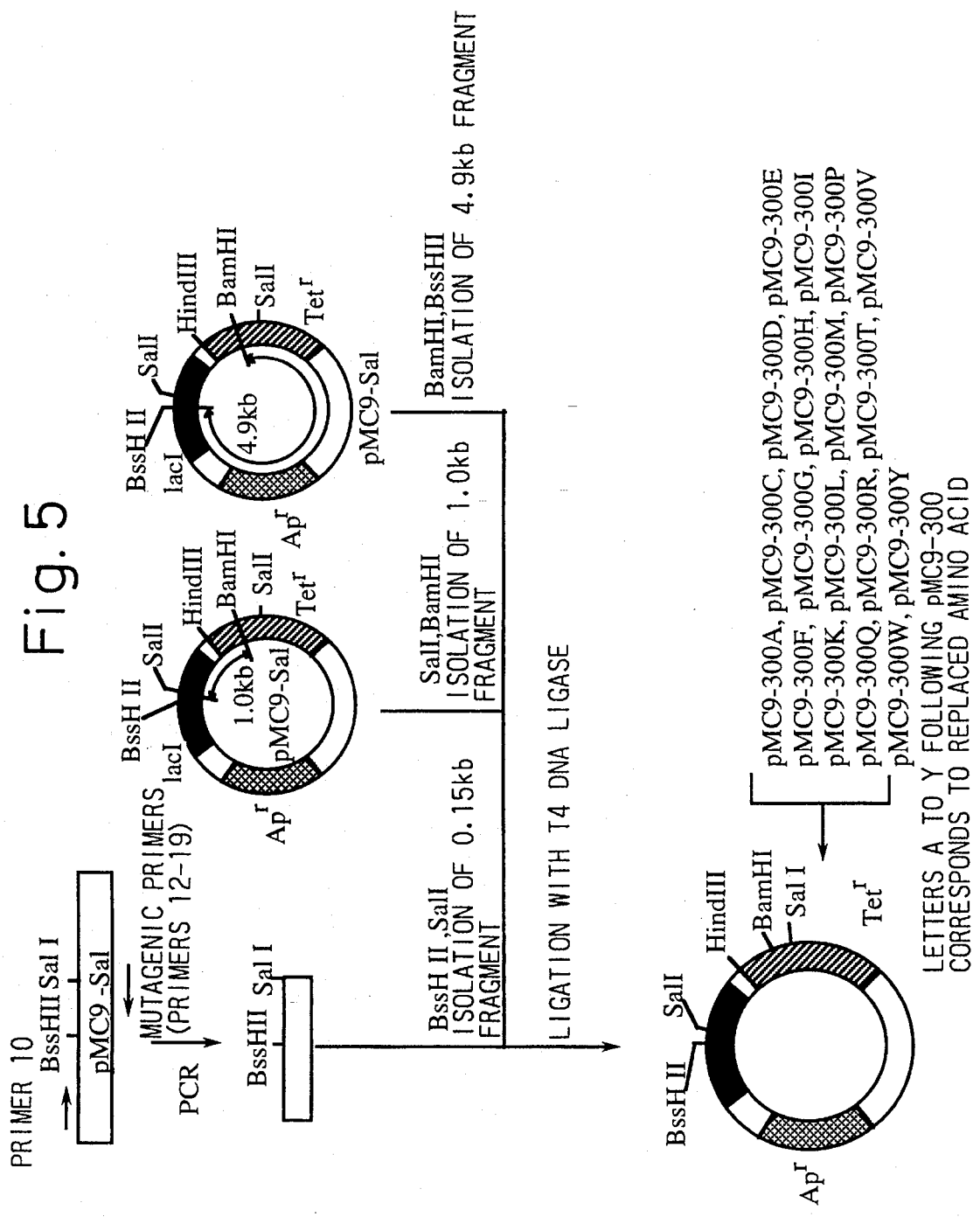

METHOD FOR CONTROLLING GENE EXPRESSION

BACKGROUND OF THE INVENTION

1. Field of the Invention

The present invention relates to a novel method for controlling gene expression using *Escherichia coli* lactose repressor gene with a temperature-sensitive mutation. The present invention also relates to a method for gene expression using said method for controlling the gene expression, and more particularly to a method for controlling gene expression by controlling a temperature for culturing host cells.

2. Related Art

An expression control gene region of *E. coli* lactose operon, i.e., a gene region from a lac gene coding for a repressor protein to promoter/operator is one of the control gene regions which is most frequently used for the expression of a gene located downstream of the control gene region. This is because, when an inducer substance such as isopropyl-β-D-thiogalactopyranoside (IPTG) exists in host cells, lactose repressor cannot bind to the lactose operator region and transcription from the lactose promoter occurs, which makes transcriptional control during the gene expression possible.

Various cloning vectors and gene expression vectors for the production of useful substances are used by virtue of the fact that a gene expression can be successfully carried out by addition of an inducer such as IPTG into a culture medium. For example, a member of the pUC series such as pUC18 etc. as a gene cloning vector, M13 phage series for determination of a nucleotide sequence of DNA, λgt11 etc. for cDNA cloning are used. Recently, this expression control system has been also used in studies using animal cells (Ulrich Deuschele et al., Proc, Natl. Acad. Sci. USA, Vol. 86, pp. 5400–5404, 1989; Mickey C. T. Hu et al., Mol. Cell. Biol. Vol. 10, pp. 6141–6151, 1990).

In addition, this expression control system has been used for the production of useful substances (Mercedes Zazo et al., Gene, Vol. 113, pp. 231–238, 1992). However, this system has drawbacks in that IPTG, an expensive inducing agent, must be added to the culture medium to induce the expression of genes. Especially, if this system is used for the production of useful substances on an industrial scale, the use of IPTG increases the production cost.

Accordingly, an industrially useful novel method for controlling the expression of a gene is urgently sought. Accordingly, regarding the expression of a desired gene, the development of a system for controlling the expression of a gene without using an expensive inducer such as IPTG, and of a method for expressing a gene using said control system are sought.

SUMMARY OF THE INVENTION

The present inventor, as a result of a search for repressor proteins in the expression control gene of *E. coli* lactose operon, found a new lactose repressor protein. This repressor protein binds the operator and inhibits the transcription at a low temperature, but is inactivated and cannot bind the operator at a high temperature, and therefore the repressor protein is a temperature-sensitive mutant repressor protein. The present invention uses the above-mentioned new repressor protein.

Accordingly, the present invention provides a lactose repressor protein wherein at least one amino acid at the position 94, 241, 265 or 300 of the wild lactose repressor is replaced with an amino acid other than that of the wild lactose repressor.

The above-mentioned replacement of amino acids includes a mutation of the 94th amino acid valine to methionine, a mutation of the 241st amino acid alanine to threonine, a mutation of the 265th amino acid glycine to aspartic acid used and/or a mutation of the 300th amino acid serine to asparagine, phenylalanine or proline. An example of the amino acid sequence of a mutated lactose repressor protein is shown in SEQ ID NO: 20.

The present invention also provides a gene coding for the above-mentioned temperature-sensitive lactose repressor protein (lactase repressor protein gene). An example of a nucleotide sequence of this gene is shown in SEQ ID NO: 20.

The present invention further provides a method for controlling the expression of a gene coding for a desired protein (desired gene) in a host cell containing said lactose repressor protein gene and said desired gene, characterized by controlling the expression of the desired gene by regulating a function of the lactose repressor protein by changing the temperature for culturing said cell.

In this method, the lactose repressor protein gene is introduced into a chromosome of the host or into an extra-chromosomal entity such as plasmid, for example, cloning vector or an expression vector. The host cells include, for example, prokaryotes, for example, bacteria such as *E. coli*, and eukaryotes, for example, lower eukaryote such as fungi, yeast, and higher eukaryote such as mammalian cells, insect cells, or the like. In the present method, the expression of a desired gene is repressed at a room temperature for example 30° C., and the expression of a desired gene is derepressed at a higher temperature, for example 35° C. or higher temperature, for example at 37° C. or higher temperature.

The present invention still further provides a method for expressing a gene coding for a desired protein (desired gene) characterized by controlling the expression of the desired gene by regulating a function of the lactose repressor protein by changing a temperature for culturing host cells transformed with an expression vector comprising the lactose repressor protein gene and the desired gene. In this method, the host cells and the control of culturing temperature are as described above.

BRIEF EXPLANATION OF THE DRAWINGS

FIG. 5 shows a process for the construction of various plasmids containing a site-directed mutation at the 300th position.

DETAILED DESCRIPTION OF THE INVENTION

Figure 1:
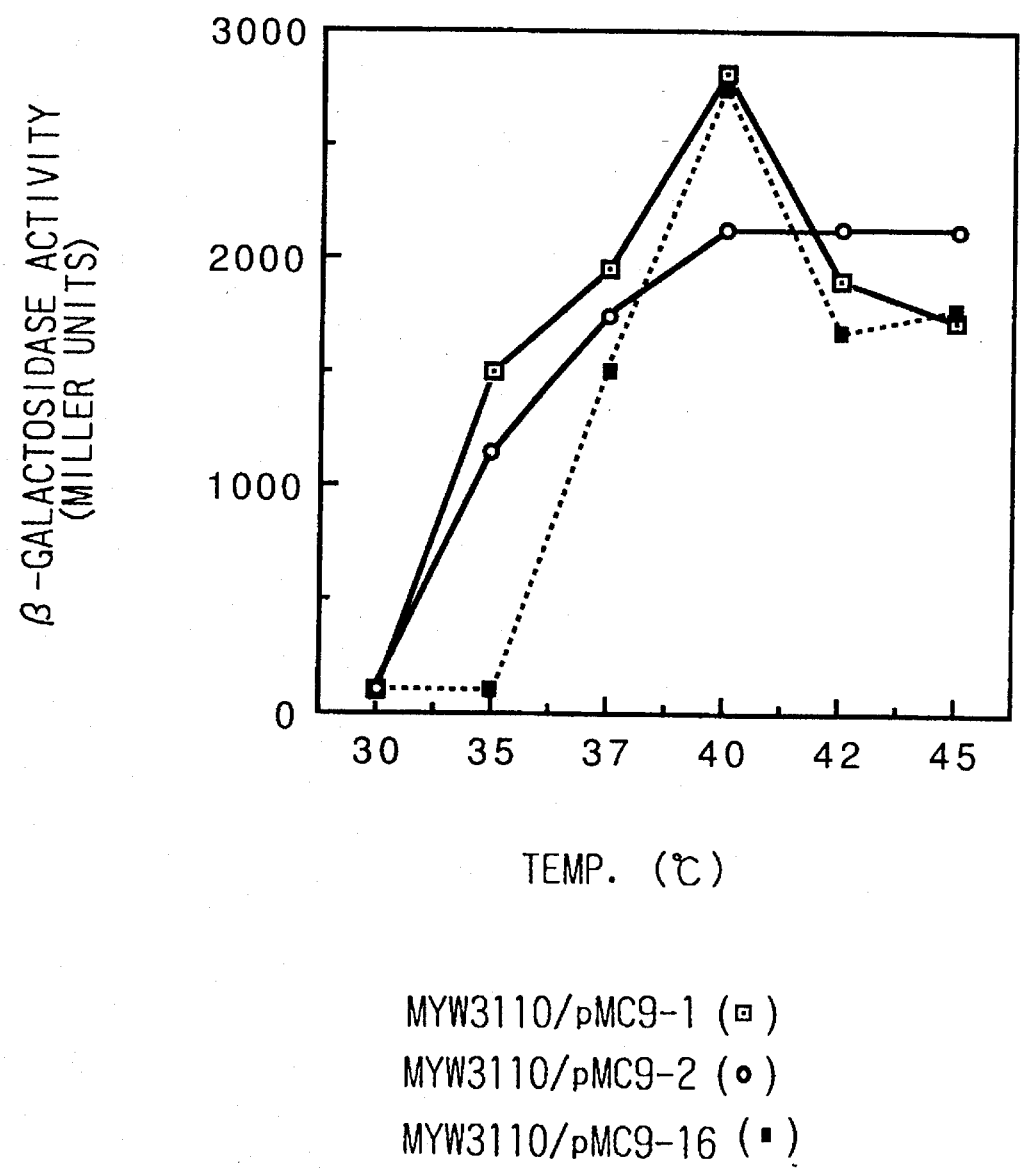
FIG. 1 is a graph showing an effect of culture temperature on β-galactosidase production.

Plasmid pMC9 carrying a lacI gene encoding a lactose repressor protein is treated with a mutagen hydroxylamine to introduce a mutation on the lacI gene. The plasmid thus treated is used to transform a lacI gene mutant MYW3110 strain derived from *E. coli* K12. The transformed cells are inoculated on an agar plates containing amplicillin and 5-bromo-4-chloro-3-indoryl-β-D-galactopyronoside (X-gal), and cultured at 38° C. overnight.

After culturing, blue colonies are selected and inoculated on the same two plates and one plate is incubated at 30° C. and another plate is incubated at 38° C., overnight. By this screening procedure, 7 temperature-sensitive mutants which show white color at 30° C. and blue color at 38° C. were obtained. To confirm that the mutations thus obtained had occurred within the lacI gene on the plasmid, the plasmids were isolated from each temperature-sensitive mutant, and nucleotide sequence of lacI gene was determined.

As a result, it was found that the 300th serine residue of the lactose repressor protein was converted to asparagine residue, the 241st alanine residue was converted to threonine residue, the 265th glycine residue was converted to aspartic acid residue, and the 94th valine residue was converted to methionine residue. The mutations at these positions are not included in sequences so far reported as temperature-sensitive mutations, and the above-mentioned mutated sequence is a novel one, isolated and identified by the present invention for the first time.

Next, these isolated lactose repressor genes with the temperature-sensitive mutations were tested to determine whether these mutated genes can be used to control the expression of a gene. First, the mutant lacI gene having the above-mentioned mutation was inserted into a plasmid having compatibility with colicin El-derived plasmid, for example pMW119, so as to construct new plasmids pY01, pY02 and pY016. Next, as an example of a protein to be expressed, a fusion protein of a human calcitonin precursor peptide may be mentioned. The plasmid pG97S4DhCT(GRRR) isolated from a strain producing the above-mentioned fusion protein is introduced by transformation into *E. coli* MYW3110/pY01, MYW3110/pY02 and MYW3110/pY016 containing the plasmid pY01, pY02 and pY016 respectively, so as to obtain transformants.

Note, *E. coli* W3110 containing plasmid pG97S4DhCT [G] which is substantially the same as the plasmid pG97S4Dh[GRRR] has been designated *Escherichia coli* SBM323 and deposited with the National Institute of Bioscience and Human Technology Agency of Industrial Science and Technology under the Budapest treaty on Aug. 8, 1991, and has the deposition No. FERM BP-3503. The difference between the plasmids pG97S4DhCT[GRRR] and pG97S4DhCT[G] is only that the pG97S4DhCT[G] encodes a fusion protein in which the desired protein has glycine at its C-terminus, while the pG97SDhCT[GRRR] encodes the fusion protein in which the desired protein has three additional arginine residues after said glycine.

The transformants thus obtained were cultured at 30° C. and then further cultured at 37° C. to test the production of protein (especially fusion protein). As a result it was found that the production of the protein was not induced at 30° C., while the production of the protein was induced at 37° C., and therefore it was proved that the repressor protein having the temperature-sensitive mutation and the gene coding therefor can be used to control the expression of a gene.

It is considered that the positions of the above-mentioned mutation are the positions on the high-dimensional structure of the lactose repressor protein, which are highly labile to changes of temperature. In other words, it is considered that the positions of the mutation are important to maintain the high-dimensional structure of the lactose repressor protein. Accordingly, it is expected that further temperature-sensitive mutants of the lactose repressor protein can be obtained by inserting other amino acid residues into the positions at which the mutation occurred.

Thus, mutant lacI genes wherein the codon for the 300th amino acid of the lactose repressor protein was replaced with a codon for one of 18 amino acids were obtained by in vitro mutagenesis, and the temperature-sensitivity of the mutant lacI genes was tested. As a result, the mutant genes wherein the codon of 300th amino acid was replaced with a codon for other amino acid, especially phenylalanine or proline exhibited the temperature sensitive phenotype.

It was confirmed that the temperature-sensitive mutation sites of the isolated repressor protein of the present invention, i.e., the amino acid residues at the 94th, 241st, 265th and 300th positions of the lactose repressor protein are imported to maintain the high-dimensional structure of the protein. Accordingly, temperature-sensitive mutation can be introduced by replacing the amino acid residues at the above-mentioned positions with other amino acid residues. In the Examples hereinafter, the production of protein was actually tested and it was shown that the repressor genes of the present invention involving the temperature-sensitive mutation can be used to control the expression of a desired gene.

Amino acid sequences of the lactose repressor proteins relating to the present inventions and nucleotide sequences therefor are shown in SEQ ID NO.: 20. Among these amino acid sequences, the amino acid sequence wherein the 94th Xaa is val, the 241st Xaa is Ala, the 265th Xaa is Gly, and the 300th Xaa is Ser is the amino acid sequence of the wild type lactose repressor protein. In one embodiment of the present invention, the 94th Xaa is Met; in another embodiment, the 241st Xaa is Thr; in another embodiment the 265th Xaa is Asp; and another embodiment the 300th Xaa is Asn, Phe or Pro.

As described above, it is reasonably considered that not only the lactose repressor proteins wherein one of the positions 94, 241, 265 and 300 is mutated, but also lactose repressor proteins wherein two positions, i.e., the positions 94 and 241, the positions 94 and 256, or the positions 94 and 300 are mutated; lactose repressor proteins wherein three positions, i.e., the positions 94, 241 and 265, the positions 94, 241 and 300, or the positions 241, 265 and 300 are mutated; as well as the lactose repressor protein wherein all four positions, i.e., the positions 94, 241, 265 and 300 are mutated, are temperature-sensitive and are within the scope of the present invention.

As can be seen from the fact that the 300th amino acid serine can be replaced with asparagine, phenylalanine or proline, the amino acid which replaces a native amino acid at a particular position is not limited to one amino acid. Namely, although the 265th native amino acid glycine can be replaced with aspartic acid; the 241st native amino acid alanine can be replaced with threonine; and the 94th native amino acid valine can be replaced with methionine, amino acids which replace the native amino acids at the above-mentioned positions are not limited to those described above.

Namely, according to the same procedure as described for the replacement at the 300th position, amino acids which replace the 265th, 241st and 94th positions can be determined. Particularly, site specific mutation is carried out to replace the native amino acids at the above-mentioned positions, and DNA encoding the site-mutated repressor protein is synthesized. Next, according to the same procedure as described for the 300th position mutation, the amino acids located at the above-mentioned positions can be replaced with an amino acid which makes the lactose repressor temperature-sensitive.

The present invention also relates to an invention of genes coding for the above-mentioned various lactose repressor proteins. These genes have various nucleotide sequences due to the degeneracy of genomic codon. These genes can be synthesized so as to have nucleotide sequences designed on the basis of the amino acid sequences. Alternatively, these genes can be obtained by site-specific mutagenesis of the codons of the DNA, which encode the native amino acids or non-native amino acids other than desired amino acids. DNA coding for lactose repressor protein having more than one mutation can be chemically synthesized, or obtained by site-specific mutations.

The present invention further provides a method for controlling the expression of a gene coding a desired protein (desired gene) using the present temperature-sensitive lactose repressor proteins. This method can be carried out by containing a temperature-sensitive lactose repressor gene and a lactose operator gene region linked to a gene encoding a desired protein (desired gene) in the same cell and controlling the culture temperature. The repressor gene and the desired gene may exist on the same gene or different genes.

For example, the repressor gene and the desired gene can exist on the same extrachromosomal gene. Here, the extrachromosomal gene means self-replicable plasmid, phage, virus etc.

Temperature-sensitive lactose repressor proteins of the present invention repress the expression of a desired gene linked to a lactose operator at a culture temperature up to 30° C., for example 20° C. to 30° C., while they do not repress the expression of the desired gene linked to the lactose operator at a culture temperature of 35° C. or more, for example, 37° C. or more. Accordingly, a desired gene can be expressed by growing host cells at a temperature of 30° C. or lower, and increasing the temperature to 35° C. or more, for example 37° C. or more.

Host cells used in the present invention may be any cells conventionally used for the expression of a desired gene by gene recombination technique. For example, prokaryotic cells, for example, bacteria such as *Escherichia coli*, Bacillus such as *Bacillus brevis*; and lower eukaryotic cells, for example, yeast such as Saccharomyces, such as *Saccharomyces cerevisiae*, alcohol-assimilating yeast such as *Pichia pastoris, Hansenula polymorpha, Candida boidinii* and further filamentous fungi such as Aspergillus can be used.

In addition, higher eukaryotic cells, for example, animal cells such as COS cells, CHO cells (Chinese Hamster Ovary Cell), BHK cells (Baby Hamster Kidney Cell), and insect cells such as SF9 cells, and the like can be used.

Although the Examples hereinafter use a lactose promoter, any other appropriate promoters can be used in the present invention. Namely, the present repressor gene can be applied to systems which control the expression of a desired gene using expression vectors or cloning vectors (for example, plasmid, phage etc.) comprising any appropriate promoter region gene and a lactose operator region gene positioned downstream of the promotor region gene. Appropriate promotor regions other than lactose promoter include tac, trc, lacUV5 etc., although they are not limited to them.

Any proteins and peptides which can be produced by gene recombination can be produced by the present method. These proteins or peptides include, for example, biologically active peptides, such as insulins, growth hormones, diuretic peptides (especially, C-type natriuretic peptides; CNP), calcitonins, parathyroid hormones (PTH1-34, PTH1-84 etc.), biologically active proteins such as cell-differentiation growth factors, cell growth inhibiting factors, and further physiologically important enzymes.

The temperature-sensitive lactose repressor protein gene of the present invention can be used by inserting it into an extrachromosomal entity such as plasmid or a chromosome of a host to control the expression of a desired gene. Examples described hereinafter use plasmids.

The present invention is very important from an industrial point of view, because the temperature-sensitive mutant lactose repressor gene provides the expression of a gene encoding a desired peptide or protein without using an expensive inducer such as IPTG.

EXAMPLES

The present invention is further explained in the following Examples, although the present invention should not be limited thereto.

Example 1.

Construction of lactose repressor mutant strain derived from *E. coli* W3110

Our purpose of this invention is to isolate temperature-sensitive mutants of the lacI gene and their application to control a desired gene expression. To isolate a lactose repressor gene (lacI gene) having a temperature-sensitive mutation, first, we constructed lacI⁻ host strain as follows. It is known that if the lactose repressor is mutated, β-galactosidase is constitutively expressed (constitutive phenotype), and as a method for isolating such a mutant, a screening method using phenyl-β-D-galactoside is known (J. H. Miller, A Short Course in Bacterial Genetics, Laboratory Manual pp. 131–134, Cold Spring Harbor Laboratory, 1992).

According to this method, cells of parent strain *E. coli* W3110 (available as ATCC 14948) were plated on agar plates containing phenyl-β-D-galactoside as the carbon source, and cultured at 37° C. for two days. After culturing, colonies were isolated and a lactose repressor mutant showing a constitutive expression of β-galactosidase was chosen and named *E. coli* MYW3110.

Example 2.

Isolation of lactose repressor gene having temperature-sensitive mutation

Plasmid pMC9 is a derivative of pBR322 and is present in *E. coli* Y1089 (Huynh, T. V. et al., (1985) DNA Cloning Vol. 1, IRL Press Limited, Oxford, England, pp. 49–78; available from Invitrogen; catalog No. 789-02).

10 μg of pMC9 was added to 1 ml of 50 mM phosphate buffer (pH 7.0) containing 100 mM NaCl, 2 mM EDTA and 1M hydroxylamine, and reaction was carried out at 65° C. for 30 minutes. The reaction mixture was dialyzed against 5 L of TE (10 mM Tris HCl, pH 8.0, 1 mM EDTA), and ethanol precipitation was carried out according to a conventional procedure, and the resulting precipitate was dissolved in 20 μl of TE. 4 μl of the solution was used to transform *E. coli* MYW3110 according to the conventional calcium chloride method.

Transformants were plated on L-agar plates (Polypepton 10 g, NaCl 5 g, yeast extract 5 g and agar 15 g in 1 l of deionized water) supplemented with 40 μg/ml 5-bromo-4-chloro-3-indoryl-β-D-galactopyranoside (X-gal) and 50 μg/ml ampicillin, and cultured at 38° C. overnight. Among the transformants, colonies providing blue color on this medium were selected, and the colonies were inoculated on two agar plates having the above-mentioned composition, and one agar plate was incubated at 30° C. overnight, and another agar plate was incubated at 38° C. overnight As a result, 7 transformants which provided white color at 30° C., and blue color at 38° C. were obtained. To confirm that the temperature-sensitive mutation exists on the lacI gene, plasmid was isolated from each transformant according to a conventional alkaline denaturation method, and the plasmid was used to again transform E. coli MYW3110 to confirm that the transformant showed the same phenotype. The plasmids were designated pMC9-1, pMC9-2, pMC9-6, pMC9-16, pMC9-17, pMC9-22 and pMC9-24.

Example 3.

Determination of position of mutation

To determine the position of the mutation on the lacI gene of the above-mentioned plasmids pMC9-1, pMC9-2, pMC9-6, pMC9-16, pMC9-17, pMC9-22 and pMC9-24, the following experiment was carried out. The plasmid was purified by ultra-centrifugation method, and sequenced using a T7 Sequencing TM kit (Pharmacia) with chemically synthesized primers. The 20 mer primers were as follow:

Primers used for sequencing
Primer 1; 5'-GCAACGCCAATCAGCAAC-3' (SEQ ID NO: 1)
Primer 2; 5'-GGGTGTCTGGTCAGAGAC-3' (SEQ ID NO: 2)
Primer 3; 5'-ATCGTTGGCAACCAGCATCGCA-3' (SEQ ID NO: 3)
Primer 4; 5'-CGCCGTCGCAAATTGTCG-3' (SEQ ID NO: 4)
Primer 5; 5'-CTCCCATGAAGACGGTACG-3' (SEQ ID NO: 5)
Primer 6; 5'-GCAATGCGCGCCATTACC-3' (SEQ ID NO: 6)
Primer 7; 5'-CATCGAATGGCGCAAAA-3' (SEQ ID NO: 7)

Taking the first "G" of the translation initiation codon GTG of the lacI gene as nucleotide number 1, the primer 1 corresponds to the nucleotide number 183 to 200, the primer 2 corresponds to the nucleotide number 448 to 465, the primer 3 corresponds to the nucleotide number 720 to 741, the primer 4 corresponds to the nucleotide number 224 to 241, the primer 5 corresponds to the nucleotide number 483 to 501, the primer 6 corresponds to the nucleotide number 757 to 774, and the primer 7 corresponds to the nucleotide number −72 to −56 upstream of the translation start codon. As upper primers the primers 1 to 3 and 7 were used, and the lower primers the primers 4 to 6 were used. The DNA sequences of the isolated genes and amino acid sequences encoded by the genes are shown in SEQ ID NO: 20.

Comparison of the mutated lacI genes isolated by the present inventors with the wild lacI gene described by J. H. Miller (A Short Course in Bacterial Genetics, Handbook Section 16, Cold Spring Harbor Laboratory 1992) is shown in Table 1. As shown in Table 1, in the plasmids pMC9-1, pMC9-17 and pMC9-24, the codon AGC coding for the 300th amino acid serine was mutated to the codon AAC coding for asparagine; in the plasmids pMC9-16 and pMC9-22, the codon GCG coding for the 241st amino acid alanine was mutated to the codon ACG coding for threonine; in the plasmid pMC9-2, the codon GGT coding for the 265th amino acid glycine was mutated to the codon GAT coding for aspartic acid; and in the plasmid pMC9-6, the codon GTG coding for the 94th amino acid valine was mutated to the codon ATG coding for methionine.

TABLE 1

Positions of mutation on temperature-sensitive lacI gene

| Plasmid | Amino acid No. | Wild type Amino acid | Codon | Mutant Amino acid | Codon |
|---|---|---|---|---|---|
| pMC9-1 pMC9-17 pMC9-24 | 300 | Serine | AGC | Asparagine | AAC |
| pMC9-16 pMC9-22 | 241 | Alanine | GCG | Threonine | ACG |
| pMC9-2 | 265 | Glycine | GGT | Aspartic acid | GAT |
| pMC9-6 | 94 | Valine | GTG | Methionine | ATG |

Various mutants of lactose repressor are reported by J. H. Miller et al., J. M. Biol. (1990) Vol. 212, pp. 295–318. The positions of the mutation providing the temperature-sensitivity of the present invention are different from those of Miller et al., and the present mutant lactose repressors are novel.

It is known that the lactose repressor has two functional domains having different functions. Namely, the N-terminal 59 amino acid residues of the protein that binds the operator DNA, and the remaining "core" region of the protein that is required for both oligomer formation and binding to an inducer such as IPTG. In the repressor gene of the present invention, mutations exist on the codons encoding the 94th, 241st, 265th and 300th amino acid residues of the lactose repressor protein. The region containing these mutations corresponds to the "core" region. Accordingly, at a higher temperature, these mutations will, with a high probability, result in the incapability of the tetramer formation or cause a structural change in the repressor protein, simulating the structure formed by binding of an inducer.

Next, the plasmids pMC9-1, pMC9-2 and pMC9-16, which have preferred properties relating to temperature-sensitive mutation, were further tested.

Example 4.

Relationship between temperature-sensitive mutant lactose repressor and culture temperature In Example 3 described above, the properties of the temperature-sensitive mutations of the lactose repressor at 30° C. representing a lower temperature and 38° C. representing a higher temperature were studied. It is considered to be further importance for determining preferable culture conditions for a transformant to determine a critical temperature below which the expression is not induced and above which the expression is induced. Therefore, an inoculum culture prepared by culturing the transformant at 30° C. was further cultured in a test culture medium at a temperature of 35° C., 37° C., 40° C., 42° C. or 45° C. to determine the above-mentioned critical temperature using as an indicator β-galactosidase activity expressed by the host chromosome.

Namely, *E. coli* MYW3110/pMC9-1, *E. coli* MYW3110/pMC9-2 and *E. coli* MYW3110/pMC9-16 were separately inoculated to 3 ml of L-medium containing 50 μg/ml ampicillin, and cultured at 30° C. overnight. The OD660 value of the culture was measured, and a volume of the culture, wherein a value of OD660 of the culture times the volume of the culture is 0.5, was inoculated to 2 ml of L-medium containing 50 μg/ml ampicillin at a temperature of 30°, 35°, 37°, 40°, 42° or 45° C. for 3 hours.

An expressed β-galactosidase activity was measured using ONPG(O-nitrophenyl-β-D-galactoside) as a substrate according to Miller et al. method (Experiment in Molecular Genetics, pp. 352–355, Cold Spring Harbor laboratory 1972). A result is shown in FIG. 1. As seen from FIG. 1, *E. coli* MYW3110/pMC9-1, *E. coli* MYW3110/pMC9-2 and *E. coli* MYW3110/pMC9-16 substantially did not produce β-galactosidase activity at 30° C. revealing that the expression of β-galactosidase gene was repressed while at a temperature of 35° C. to 37° C., the expression of β-galactosidase gene occurred.

The critical temperature at which the expression of a gene is induced, i.e., the temperature at which the lactose repressor becomes unfunctional is 35° C. for *E. coli* MYW3110/pMC9-1 and *E. coli* MYW3110/pMC9-2, and 37° C. for *E. coli* MYW3110/pMC9-16. All *E. coli* strains described above induced the maximum expression of the lacZ gene at a temperature of 40° C. Accordingly, the present temperature-sensitive mutant lactose repressor gene can be satisfactorily used for the expression of a desired gene at 37° C., which is considered to be the best temperature for the growth of host cells and is used for experimental or large scale culture of the host cells.

Example 5.

Control of gene expression using temperature-sensitive mutant lactose repressor gene for production of useful fusion protein Example 4 described above is directed to the control of the expression of β-galactosidase gene on a host chromosome using the temperature-sensitive mutant lactose repressor gene. The present Example 5 is directed to another object of the present invention, i.e., a method for the expression of a desired gene by controlling a culture temperature for a transformant using the temperature-sensitive mutant lactose repressor.

Namely, the present inventors tried to use the present temperature-sensitive mutant lactose repressor gene to control the expression of a fusion protein comprising a β-galactosidase derivative and a human calcitonin precursor peptide as an example of a desired protein by an expression plasmid comprising a promoter/operator region of the lactose operon as an expression control gene region and a gene coding for said fusion protein downstream of the expression control gene region.

Figure 2:
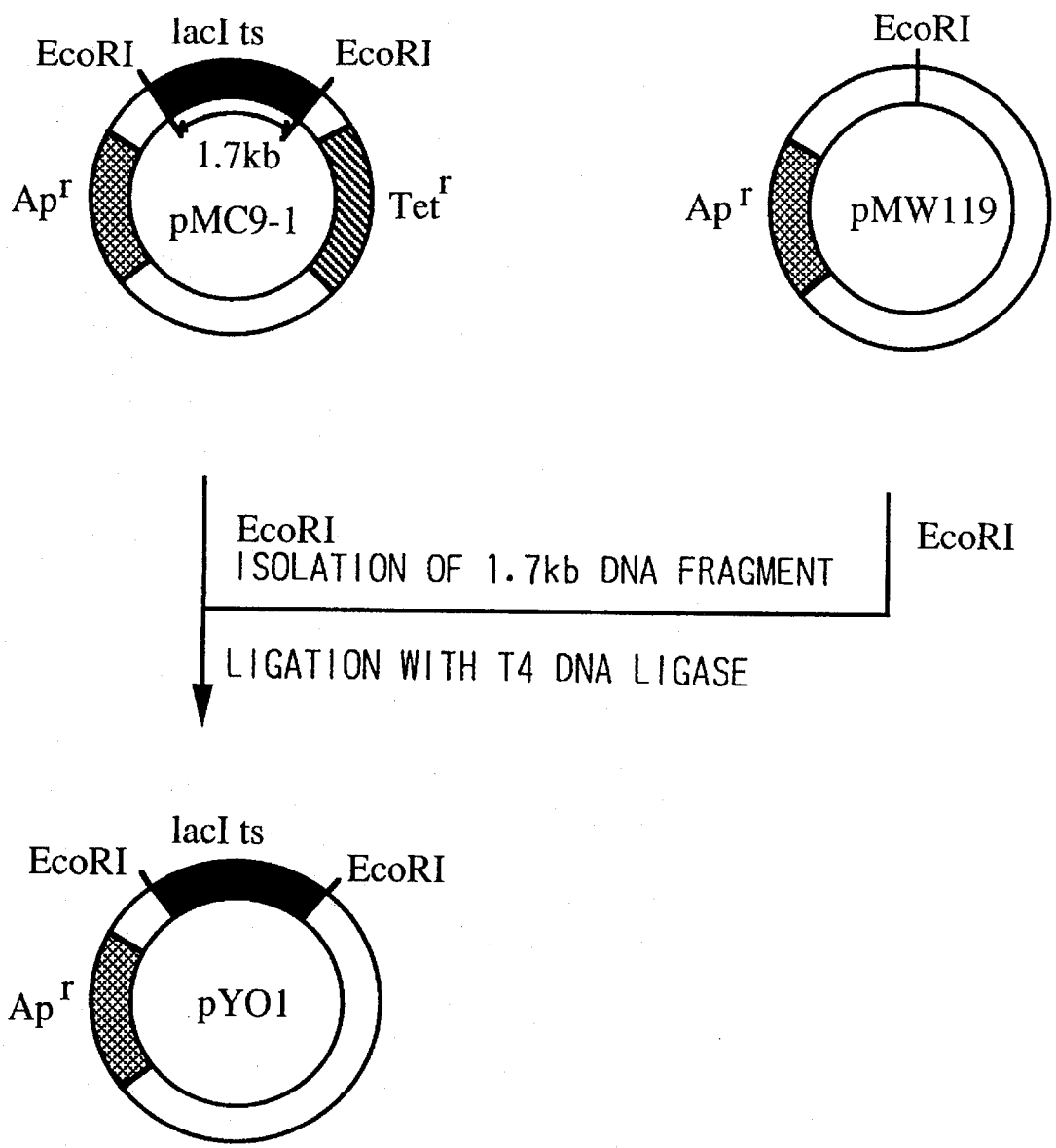
FIG. 2 shows a process for the construction of plasmid pY01 from plasmids pMC9-1 and pMW119.

First, the plasmid pMC9-1 was cleaved with EcoRI to isolate a temperature-sensitive mutant lactose repressor gene region of 1.7 kb, which was then inserted into the EcoRI site of pMW119 (low copy number plasmid having an origin of replication derived from pSC101, Nippon Gene) so as to construct pY01 (FIG. 2). According to the same procedure as described above, the plasmids pMC9, pMC9-2 and pMC9-16 were used to construct pYOW, pY02 and pY016.

Plasmid pG97S4DhCT[GRRR] encoding a fusion protein comprising *E. coli* β-galactosidase derivative and human calcitonin precursor peptide downstream of the lactose promoter/operator (lacPO) was used to transform *E. coli* cells containing the plasmid pMC9, pMC9-2 or pMC9-16 constructed above to obtain ampicillin and tetracycline resistant *E. coli* MYW3110/pG97S4DhCT[GRRR], pYOW; *E. coli* MYW3110/pG97S4DhCT[GRRR], pY01; *E. coli* MYW3110/pG97S4DhCT[GRRR], pY02; and *E. coli* MYW3110/pG97S4DhCT[GRRR], pY016.

These strains were cultured an L-medium supplemented with 50 μg/ml ampicillin and 10 μg/ml tetracycline at 30° C. overnight to prepare an inoculum culture, and the inoculum culture was inoculated to two media having the same composition as described above in an amount of 5% relating to the medium. One of the media was incubated at 30° C. for 15 hours, and another medium was incubated at 37° C. for 15 hours. *E. coli* MYW 3110/pG974DhCT[GRRR], pYOW having the wild type lactose repressor gene was induced by adding IPTG to a final concentration of 5 mM IPTG. After culturing, the culture medium was centrifuged, and the fusion protein produced in the cultured cells was measured by SDS-16% PAGE (sodium dodecyl sulfate 16% polyacrylamide gel electrophoresis) to compare the expression of the fusion protein at different temperatures. A result is shown in FIG. 3.

Figure 3:
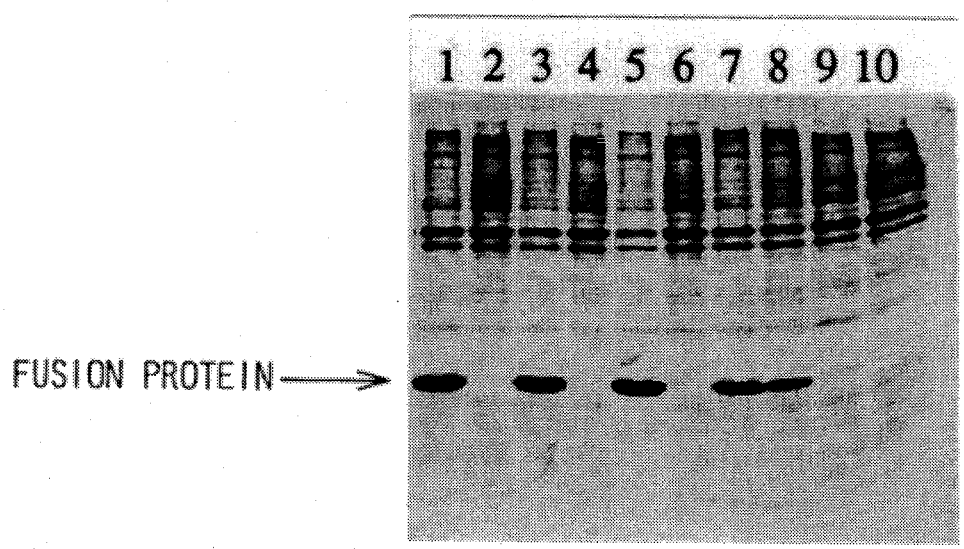
FIG. 3 shows a Sodium Dodecyl Sulfate gel electrophoresis showing the effects of culture temperature and an inducer on the production of a protein.

As seen from FIG. 3, *E. coli* MYW 3100/pG97S4DhCT[GRRR], pYOW having the wild type lactose repressor gene produced the fusion protein only when IPTG was added. *E. coli* MYW 3110/pG97SDhCT[GRRR], pY01; *E. coli* MYW 3110/pG97S4DhCT[GRRR], pY03; and *E. coli* MYW 3110/pG97S4DhCT[GRRR], pY016 did not express the fusion protein when they were cultured at 30° C., but they expressed the fusion protein when they were cultured at 37° C., in an amount comparable to the amount the strain having the wild type lactose repressor expressed when it was induced with IPTG.

Accordingly, it was confirmed that the temperature-sensitive mutant lactose repressor gene of the present invention can be used to control the expression of a fusion protein by an expression plasmid comprising a promoter/operator region of the lactose operon as an expression control gene region and a gene coding for the fusion protein comprising β-galactosidase derivative and human calcitonin precursor peptide downstream of the expression control region.

Accordingly, the temperature-sensitive mutant lactose repressor genes of the present invention can be used to control the expression in an expression system comprising a combination of the lactose operator gene region and a lactose repressor gene.

Example 6

Effect of amino acid replacement at mutation site on temperature-sensitivity

It is considered that the amino acid positions 94, 241, 265 and 300 identified by the present inventors as temperature-sensitive mutation positions of the lactose repressor are important to maintain the structure of the repressor protein. It is reasonably considered that mutant proteins wherein the amino acid residues at the mutation sites of the repressor protein are replaced with amino acid residues other than those identified in Example 3 exhibit temperature-sensitivity depending on the kind of the amino acid.

Accordingly, 18 genes coding for mutant lactose repressor proteins the 300th position of which is replaced with one of 18 different amino acids were constructed and characterized. Namely, a site-directed mutation was introduced into the lactose repressor gene by PCR (polymerase chain reaction). First, plasmid pMC9-SalI wherein a SalI restriction site was introduced into the lacI gene was constructed by changing the 903rd nucleotide "G" of the lacI gene to "C", without changing amino acid.

Primers 8 and 9 designed to provide a SalI cleavage site at the 5'-side were chemically synthesized. The primer 9 in combination with primer 10 was used in PCR using pMC9-1 as template DNA to prepare DNA fragment A; and the primer 8 in combination of primer 11 was used in PCR using pMC9-1 as template DNA to prepare DNA fragment B.

Primer 8; 5'-GGG GCA AAC CAA CGT CGA CCG CTT GCT GCA (SalI)  (SEQ ID NO: 8)

Primer 9; 5'-TGC AGC AAG CGG TCG ACG TTG GTT TGC CCC (SalI)  (SEQ ID NO: 9)

Primer 10; 5'-GGG AAT AAG GGC GAC ACG GA  (SEQ ID NO: 10)

Primer 11; 5'-CAC GGT GCC TGA CTG CGT T  (SEQ ID NO: 11)

Figure 4:
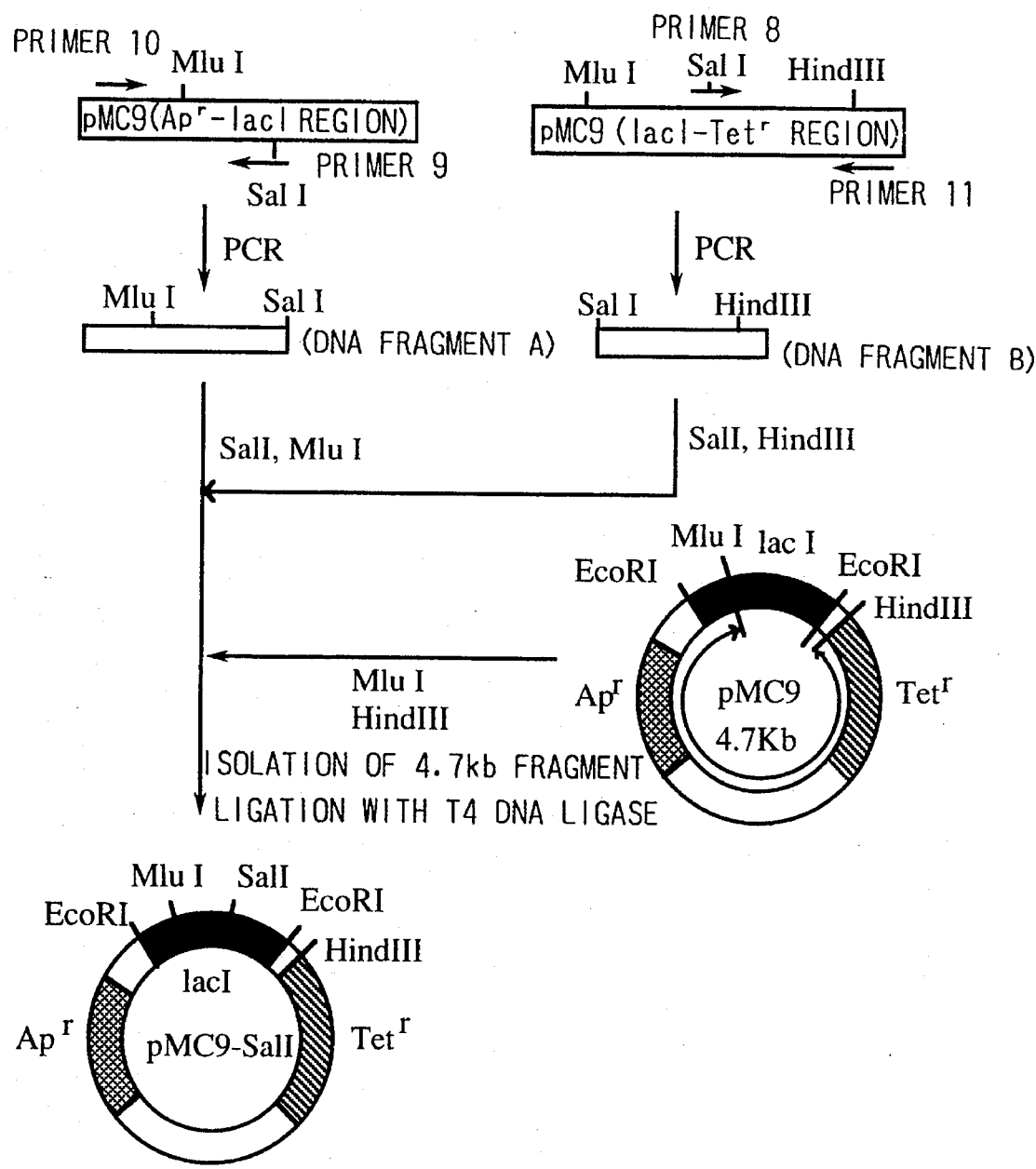
FIG. 4 shows a process for the construction of plasmid pMC9-SalI.

The PCR was carried out in 50 µl of a reaction mixture comprising 1 µmol primers, 1 µg template DNA, 50 mM KCl, 10 mM Tris-HCl, pH 8.3, 1.5 mM MgCl$_2$, 0.01% reaction mixture was used to transform *E. coli* MYW 3110, which was then plated on L-agar plate containing 50 µg/ml ampicillin, and transformants were cultured 30° C. overnight so as to construct *E. coli* MTW 3110/pMC9-SalI (FIG. 4).

Next, to introduce a mutation to the 300th amino acid position, primers 12 to 19 were synthesized and used in combination with primer 10 to carry out PCR using pMC9 as template DNA.

Nucleotide sequences of primers used to introduce mutations

Primer 12; 5'-AAG CGG TCG TCG AC A C(AGC) G GTT TGC CCC (SalI)   Amino acids replaced; Cys, Arg, Gly   (SEQ ID NO: 12)

Primer 13; 5'-AAG CGG TCG AC C T(GCT) G GTT TGC CCC (SalI)   Amino acids replaced; Glu, Gln, Lys   (SEQ ID NO: 13)

Primer 14; 5'-AAG GCG TCG AC CA(ACT) G GTT TGC CCC (SalI)   Amino acids replaced; Met, Val, Leu   (SEQ ID NO: 14)

Primer 15; 5'-AAG CGG TCG AC A G(CGT) G GTT TGC CCC (SalI)   Amino acids replaced; Thr, Pro, Ala   (SEQ ID NO: 15)

Primer 16; 5'-AAG CGG TCG AC G T(ACG) G GTT TGC CCC (SalI)   Amino acids replaced; His, Asp, Tyr   (SEQ ID NO: 16)

Primer 17; 5'-AAG CGG TCG AC G AA G GTT TGC CCC (SalI)   Amino acid replaced; Phe   (SEQ ID NO: 17)

Primer 18; 5'-AAG CGG TCG AC C CA G GTT TGC CCC (SalI)   Amino acid replaced; Trp   (SEQ ID NO: 18)

Primer 19; 5'-AAG CGG TCG AC T AT G GTT TGC CCC (SalI)   Amino acid replaced; Ile   (SEQ ID NO: 19)

☐ Codon for the 300th amino acid ( ) Mixed nucleotides gelatin, 200 µM dNTP (mixture of dATP, dGTP, dCTP and dTTP) to which 2.5 units of Taq DNA polymerase was added by 30 cycles of 94° C. for one minute, 72° C. for two minutes and 55° C. for two minutes. The resulting DNA fragment A was cleaved with restriction enzymes MluI and SalI, and the resulting DNA fragment B was cleaved with restriction enzymes SalI and HindIII.

DNA fragments thus obtained were mixed with a 4.7 kb DNA fragment prepared by cleaving pMC9 with MluI and HindIII, and they were ligated using T4 DNA ligase. The Each DNA fragment prepared by PCR was cleaved with BssHII and SalI so as to isolate a fragment of 0.15 kb, which was then mixed with a 1.0 kb SalI-BamHI fragment and a 4.9 kb BamHI-BssHII fragment of pMC9-SalI, and they were ligated with T4 DNA ligase. The reaction mixture was used to transform *E. coli* MYW 3110, which was then plated on an L-agar plate containing 50 µg/ml ampicillin, and cultured at 30° C. overnight. From the transformants thus obtained, plasmids pMC9-300A to pMC9-300Y (see, FIG. 5) were isolated, and sequenced according to the same produce as described in Example 3, and it was comfirmed that correct codon encoding an intended amino acid was introduced to the intended mutation site.

The transformants thus obtained were plated on an agar plate containing X-gal and ampicillin, and after culturing at 30° C. and 37° C. overnight, the color of the colonies developed was observed. As a result, the colonies of *E. coli* MYW3110/pMC9-300F and *E. coli* MYW 3110/pMC9-300P having a mutant lacI gene into which codons for phenylalanine and proline as 300th amino acid, respectively, were white for the 30° C. culture, and blue for the 37° C. culture.

Accordingly, it was confirmed that amino acids other than the asparagine identified as mutated amino acid in Example 3, i.e., phenylalanine and proline provide temperature-sensitive mutation, and it was proved that amino acid replacement at this site provides new temperature-sensitive mutation.

Therefore, in addition to the 300th position, replacement of amino acid at one or more of the positions 94, 241 and 265 with an amino acid other than those identified in Example 3 provide temperature-sensitive lactose repressors, and therefore such mutant lactose repressors are included in the present invention. In addition, gene coding for said proteins or peptides, a method for controlling gene expression using said gene, and a method for the expression of a desired gene using said method are included in the present invention.

The temperature-sensitive mutant repressor genes of the present invention provide the expression of a gene coding for a desired protein without using an expensive inducer such as IPTG etc., and therefore are useful for research and cloning of a desired gene, and for mass-production of the desired protein from an industrial point of view.

*Escherichia coli* SBM 323 was deposited with the National Institute of Bioscience and Technology (former Fermentation Research Institute Agency of Industrial Science and Technology), 1–3, Higashi 1-chome, Tsukubashi, Ibaraki-ken, 305, Japan, under the Budapest treaty on Aug. 8, 1991, as No, FERM BP-3503.

---

We claim:

1. A lactose repressor protein of *E. coli* wherein at least one amino acid at the position of 94, 241, 265 or 300 in the wild lactose repressor is replaced with an amino acid other than that of the wild lactose repressor.

2. A lactose repressor protein according to claim 1, wherein the 94th amino acid is methionine.

3. A lactose repressor protein according to claim 1, wherein the 241st amino acid is threonine.

4. A lactose repressor protein according to claim 1, wherein the 265th amino acid is aspartic acid.

5. A lactose repressor protein according to claim 1, wherein the 300th amino acid is asparagine, phenylalanine or proline.

6. A lactose repressor protein of *E. coli* having an amino acid sequence shown in SEQ ID NO. 20 with proviso that the amino acid sequence wherein the 94th Xaa is Val, the 241st Xaa is Ala, the 265th Xaa is Gly, and the 300th Xaa is Ser is excluded.

7. A gene coding for a lactose repressor protein *E. coli* wherein at least one amino acid at the position 94, 241, 265 or 300 in the wild lactose repressor is replaced with an amino acid other than that of the wild lactose repressor.

8. A gene according to claim 7, wherein the 94th amino acid is methionine.

9. A gene according to claim 7, wherein the 241th amino acid is threonine.

10. A gene according to claim 7, wherein the 265th amino acid is aspartic acid.

11. A gene according to claim 7, wherein the 300th amino acid is asparagine, phenylalanine or proline.

12. A gene coding for a lactose repressor protein of *E. coli* having an amino acid sequence shown in SEQ ID NO. 20 with proviso that the amino acid sequence wherein the 94th Xaa is Val, the 241st Xaa is Ala, the 265th Xaa is Gly, and the 300th Xaa is Ser is excluded.

13. A method for controlling the expression of a desired gene coding for a desired protein containing a lactose repressor protein gene of *E. coli* and said desired gene, comprising controlling the expression of the desired gene by regulating the function of the lactose repressor protein by changing the temperature for culturing said host cell.

14. A method according to claim 13, wherein the lactose repressor protein gene is inserted into a plasmid comprising the desired gene or into a host chromosome.

15. A method according to claim 13, wherein the lactose repressor gene is inserted into a cloning vector comprising the desired gene or into an expression vector.

16. A method according to any one of claims 13 to 15, wherein the host cell is mammalian cell, prokaryotic cell, fungus, yeast or insect cell.

17. A method according to claim 13, wherein a gene coding for a lactose repressor protein having temperature-sensitive mutation which expresses a gene at 35° C. or higher temperature is used.

18. A method according to claim 17, wherein a gene coding for a lactose repressor having temperature-sensitive mutation which expresses a gene at 37° C. or higher temperature is used.

19. A method for expressing a desired gene coding for a desired protein comprising controlling the expression of the desired gene by regulating the function of the lactose repressor protein of *E. coli* by changing the temperature for culturing host cells transformed with an expression vector comprising the lactose repressor protein gene and the desired gene.

20. A method according to claim 19, wherein the host cell is mammalian cell, prokaryotic cell, fungus, yeast or insect cell.

21. A method according to claim 19, wherein a gene coding for a lactose repressor protein having temperature sensitive mutation capable of expressing a gene at 35° C. or higher temperature is used.

22. A method according to claim 21, wherein a gene coding for a lactose repressor having temperature sensitive mutation capable of expressing a gene at 37° C. or higher temperature.

\* \* \* \* \*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:1:

GCAACGCCAA TCAGCAAC                                                          1 8

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:2:

GGGTGTCTGG TCAGAGAC                                                          1 8

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:3:

ATCGTTGGCA ACCAGCATCG CA                                                22

( 2 ) INFORMATION FOR SEQ ID NO:4:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Synthetic"

( x i ) SEQUENCE DESCRIPTION: SEQ ID NO:4:

CGCCGTCGCA AATTGTCG                                                     18

( 2 ) INFORMATION FOR SEQ ID NO:5:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Synthetic"

( x i ) SEQUENCE DESCRIPTION: SEQ ID NO:5:

CTCCCATGAA GACGGTACG                                                    19

( 2 ) INFORMATION FOR SEQ ID NO:6:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Synthetic"

( x i ) SEQUENCE DESCRIPTION: SEQ ID NO:6:

GCAATGCGCG CCATTACC                                                     18

( 2 ) INFORMATION FOR SEQ ID NO:7:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Synthetic"

( x i ) SEQUENCE DESCRIPTION: SEQ ID NO:7:

CATCGAATGG CGCAAAA                                                      17

( 2 ) INFORMATION FOR SEQ ID NO:8:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Synthetic"

( x i ) SEQUENCE DESCRIPTION: SEQ ID NO:8:

GGGGCAAACC AACGTCGACC GCTTGCTGCA                                     30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:9:

TGCAGCAAGC GGTCGACGTT GGTTTGCCCC                                     30

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:10:

GGGAATAAGG GCGACACGGA                                                20

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:11:

CACGGTGCCT GACTGCGTT                                                 19

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:12:

AAGCGGTCGA CACVGGTTTG CCCC                                           24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:13:

AAGCGGTCGA CCTBGGTTTG CCCC 24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:14:

AAGCGGTCGA CCAHGGTTTG CCCC 24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:15:

AAGCGGTCGA CAGBGGTTTG CCCC 24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:16:

AAGCGGTCGA CGTVGGTTTG CCCC 24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:17:

AAGCGGTCGA CGAAGGTTTG CCCC 24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:18:

AAGCGGTCGA CCCAGGTTTG CCCC                                                                                   24

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic"

( x i ) SEQUENCE DESCRIPTION: SEQ ID NO:19:

AAGCGGTCGA CTATGGTTTG CCCC                                                                                   24

( 2 ) INFORMATION FOR SEQ ID NO:20:

( i ) SEQUENCE CHARACTERISTICS:
        ( A ) LENGTH: 1083 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i x ) FEATURE:
        ( A ) NAME/KEY: CDS
        ( B ) LOCATION: 1..1080

( i x ) FEATURE:
        ( A ) NAME/KEY: misc_feature
        ( B ) LOCATION: 280..282
        ( D ) OTHER INFORMATION: /note= "May be Val or Met"

( i x ) FEATURE:
        ( A ) NAME/KEY: misc_feature
        ( B ) LOCATION: 721..723
        ( D ) OTHER INFORMATION: /note= "May be Ala or Thr"

( i x ) FEATURE:
        ( A ) NAME/KEY: misc_feature
        ( B ) LOCATION: 793..795
        ( D ) OTHER INFORMATION: /note= "May be Gly or Asp"

( i x ) FEATURE:
        ( A ) NAME/KEY: misc_feature
        ( B ) LOCATION: 898..900
        ( D ) OTHER INFORMATION: /note= "May be Ser, Asn, Phe, or
            Pro"

( x i ) SEQUENCE DESCRIPTION: SEQ ID NO:20:

```
GTG  AAA  CCA  GTA  ACG  TTA  TAC  GAT  GTC  GCA  GAG  TAT  GCC  GGT  GTC  TCT        48
Val  Lys  Pro  Val  Thr  Leu  Tyr  Asp  Val  Ala  Glu  Tyr  Ala  Gly  Val  Ser
 1             5                        10                       15

TAT  CAG  ACC  GTT  TCC  CGC  GTG  GTG  AAC  CAG  GCC  AGC  CAC  GTT  TCT  GCG        96
Tyr  Gln  Thr  Val  Ser  Arg  Val  Val  Asn  Gln  Ala  Ser  His  Val  Ser  Ala
                  20                       25                       30

AAA  ACG  CGG  GAA  AAA  GTG  GAA  GCG  GCG  ATG  GCG  GAG  CTG  AAT  TAC  ATT       144
Lys  Thr  Arg  Glu  Lys  Val  Glu  Ala  Ala  Met  Ala  Glu  Leu  Asn  Tyr  Ile
             35                       40                       45

CCC  AAC  CGC  GTG  GCA  CAA  CAA  CTG  GCG  GGC  AAA  CAG  TCG  TTG  CTG  ATT       192
Pro  Asn  Arg  Val  Ala  Gln  Gln  Leu  Ala  Gly  Lys  Gln  Ser  Leu  Leu  Ile
        50                       55                       60

GGC  GTT  GCC  ACC  TCC  AGT  CTG  GCC  CTG  CAC  GCG  CCG  TCG  CAA  ATT  GTC       240
Gly  Val  Ala  Thr  Ser  Ser  Leu  Ala  Leu  His  Ala  Pro  Ser  Gln  Ile  Val
 65                       70                       75                       80

GCG  GCG  ATT  AAA  TCT  CGC  GCC  GAT  CAA  CTG  GGT  GCC  AGC  NNN  GTG  GTG       288
Ala  Ala  Ile  Lys  Ser  Arg  Ala  Asp  Gln  Leu  Gly  Ala  Ser  Xaa  Val  Val
                  85                       90                       95
```

| | | | | | | | | | | | | | | | | |
|---|---|---|---|---|---|---|---|---|---|---|---|---|---|---|---|---|
| TCG | ATG | GTA | GAA | CGA | AGC | GGC | GTC | GAA | GCC | TGT | AAA | GCG | GCG | GTG | CAC | 336 |
| Ser | Met | Val | Glu | Arg | Ser | Gly | Val | Glu | Ala | Cys | Lys | Ala | Ala | Val | His | |
| | | | 100 | | | | | 105 | | | | | 110 | | | |
| AAT | CTT | CTC | GCG | CAA | CGC | GTC | AGT | GGG | CTG | ATC | ATT | AAC | TAT | CCG | CTG | 384 |
| Asn | Leu | Leu | Ala | Gln | Arg | Val | Ser | Gly | Leu | Ile | Ile | Asn | Tyr | Pro | Leu | |
| | | 115 | | | | | 120 | | | | | 125 | | | | |
| GAT | GAC | CAG | GAT | GCC | ATT | GCT | GTG | GAA | GCT | GCC | TGC | ACT | AAT | GTT | CCG | 432 |
| Asp | Asp | Gln | Asp | Ala | Ile | Ala | Val | Glu | Ala | Ala | Cys | Thr | Asn | Val | Pro | |
| | 130 | | | | | 135 | | | | | 140 | | | | | |
| GCG | TTA | TTT | CTT | GAT | GTC | TCT | GAC | CAG | ACA | CCC | ATC | AAC | AGT | ATT | ATT | 480 |
| Ala | Leu | Phe | Leu | Asp | Val | Ser | Asp | Gln | Thr | Pro | Ile | Asn | Ser | Ile | Ile | |
| 145 | | | | | 150 | | | | | 155 | | | | | 160 | |
| TTC | TCC | CAT | GAA | GAC | GGT | ACG | CGA | CTG | GGC | GTG | GAG | CAT | CTG | GTC | GCA | 528 |
| Phe | Ser | His | Glu | Asp | Gly | Thr | Arg | Leu | Gly | Val | Glu | His | Leu | Val | Ala | |
| | | | | 165 | | | | | 170 | | | | | 175 | | |
| TTG | GGT | CAC | CAG | CAA | ATC | GCG | CTG | TTA | GCG | GGC | CCA | TTA | AGT | TCT | GTC | 576 |
| Leu | Gly | His | Gln | Gln | Ile | Ala | Leu | Leu | Ala | Gly | Pro | Leu | Ser | Ser | Val | |
| | | | 180 | | | | | 185 | | | | | 190 | | | |
| TCG | GCG | CGT | CTG | CGT | CTG | GCT | GGC | TGG | CAT | AAA | TAT | CTC | ACT | CGC | AAT | 624 |
| Ser | Ala | Arg | Leu | Arg | Leu | Ala | Gly | Trp | His | Lys | Tyr | Leu | Thr | Arg | Asn | |
| | | 195 | | | | | 200 | | | | | 205 | | | | |
| CAA | ATT | CAG | CCG | ATA | GCG | GAA | CGG | GAA | GGC | GAC | TGG | AGT | GCC | ATG | TCC | 672 |
| Gln | Ile | Gln | Pro | Ile | Ala | Glu | Arg | Glu | Gly | Asp | Trp | Ser | Ala | Met | Ser | |
| | 210 | | | | | 215 | | | | | 220 | | | | | |
| GGT | TTT | CAA | CAA | ACC | ATG | CAA | ATG | CTG | AAT | GAG | GGC | ATC | GTT | CCC | ACT | 720 |
| Gly | Phe | Gln | Gln | Thr | Met | Gln | Met | Leu | Asn | Glu | Gly | Ile | Val | Pro | Thr | |
| 225 | | | | | 230 | | | | | 235 | | | | | 240 | |
| NNN | ATG | CTG | GTT | GCC | AAC | GAT | CAG | ATG | GCG | CTG | GGC | GCA | ATG | CGC | GCC | 768 |
| Xaa | Met | Leu | Val | Ala | Asn | Asp | Gln | Met | Ala | Leu | Gly | Ala | Met | Arg | Ala | |
| | | | | 245 | | | | | 250 | | | | | 255 | | |
| ATT | ACC | GAG | TCC | GGG | CTG | CGC | GTT | NNN | GCG | GAT | ATC | TCG | GTA | GTG | GGA | 816 |
| Ile | Thr | Glu | Ser | Gly | Leu | Arg | Val | Xaa | Ala | Asp | Ile | Ser | Val | Val | Gly | |
| | | | 260 | | | | | 265 | | | | | 270 | | | |
| TAC | GAC | GAT | ACC | GAA | GAC | AGC | TCA | TGT | TAT | ATC | CCG | CCG | TCA | ACC | ACC | 864 |
| Tyr | Asp | Asp | Thr | Glu | Asp | Ser | Ser | Cys | Tyr | Ile | Pro | Pro | Ser | Thr | Thr | |
| | | 275 | | | | | 280 | | | | | 285 | | | | |
| ATC | AAA | CAG | GAT | TTT | CGC | CTG | CTG | GGG | CAA | ACC | NNN | GTG | GAC | CGC | TTG | 912 |
| Ile | Lys | Gln | Asp | Phe | Arg | Leu | Leu | Gly | Gln | Thr | Xaa | Val | Asp | Arg | Leu | |
| | 290 | | | | | 295 | | | | | 300 | | | | | |
| CTG | CAA | CTC | TCT | CAG | GGC | CAG | GCG | GTG | AAG | GGC | AAT | CAG | CTG | TTG | CCC | 960 |
| Leu | Gln | Leu | Ser | Gln | Gly | Gln | Ala | Val | Lys | Gly | Asn | Gln | Leu | Leu | Pro | |
| 305 | | | | | 310 | | | | | 315 | | | | | 320 | |
| GTC | TCA | CTG | GTG | AAA | AGA | AAA | ACC | ACC | CTG | GCG | CCC | AAT | ACG | CAA | ACC | 1008 |
| Val | Ser | Leu | Val | Lys | Arg | Lys | Thr | Thr | Leu | Ala | Pro | Asn | Thr | Gln | Thr | |
| | | | | 325 | | | | | 330 | | | | | 335 | | |
| GCC | TCT | CCC | CGC | GCG | TTG | GCC | GAT | TCA | TTA | ATG | CAG | CTG | GCA | CGA | CAG | 1056 |
| Ala | Ser | Pro | Arg | Ala | Leu | Ala | Asp | Ser | Leu | Met | Gln | Leu | Ala | Arg | Gln | |
| | | | 340 | | | | | 345 | | | | | 350 | | | |
| GTT | TCC | CGA | CTG | GAA | AGC | GGG | CAG | TGA | | | | | | | | 1083 |
| Val | Ser | Arg | Leu | Glu | Ser | Gly | Gln | | | | | | | | | |
| | | 355 | | | | | 360 | | | | | | | | | |

( 2 ) INFORMATION FOR SEQ ID NO:21:

( i ) SEQUENCE CHARACTERISTICS:
        ( A ) LENGTH: 360 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| | | | | | | | | | | | | | | | |
|---|---|---|---|---|---|---|---|---|---|---|---|---|---|---|---|
| Val | Lys | Pro | Val | Thr | Leu | Tyr | Asp | Val | Ala | Glu | Tyr | Ala | Gly | Val | Ser |
| 1 | | | | 5 | | | | | 10 | | | | | 15 | |
| Tyr | Gln | Thr | Val | Ser | Arg | Val | Val | Asn | Gln | Ala | Ser | His | Val | Ser | Ala |
| | | | 20 | | | | | 25 | | | | | 30 | | |
| Lys | Thr | Arg | Glu | Lys | Val | Glu | Ala | Ala | Met | Ala | Glu | Leu | Asn | Tyr | Ile |
| | | 35 | | | | | 40 | | | | | 45 | | | |
| Pro | Asn | Arg | Val | Ala | Gln | Gln | Leu | Ala | Gly | Lys | Gln | Ser | Leu | Leu | Ile |
| | 50 | | | | | 55 | | | | | 60 | | | | |
| Gly | Val | Ala | Thr | Ser | Ser | Leu | Ala | Leu | His | Ala | Pro | Ser | Gln | Ile | Val |
| 65 | | | | | 70 | | | | | 75 | | | | | 80 |
| Ala | Ala | Ile | Lys | Ser | Arg | Ala | Asp | Gln | Leu | Gly | Ala | Ser | Xaa | Val | Val |
| | | | | 85 | | | | | 90 | | | | | 95 | |
| Ser | Met | Val | Glu | Arg | Ser | Gly | Val | Glu | Ala | Cys | Lys | Ala | Ala | Val | His |
| | | | 100 | | | | | 105 | | | | | 110 | | |
| Asn | Leu | Leu | Ala | Gln | Arg | Val | Ser | Gly | Leu | Ile | Ile | Asn | Tyr | Pro | Leu |
| | | 115 | | | | | 120 | | | | | 125 | | | |
| Asp | Asp | Gln | Asp | Ala | Ile | Ala | Val | Glu | Ala | Ala | Cys | Thr | Asn | Val | Pro |
| | 130 | | | | | 135 | | | | | 140 | | | | |
| Ala | Leu | Phe | Leu | Asp | Val | Ser | Asp | Gln | Thr | Pro | Ile | Asn | Ser | Ile | Ile |
| 145 | | | | | 150 | | | | | 155 | | | | | 160 |
| Phe | Ser | His | Glu | Asp | Gly | Thr | Arg | Leu | Gly | Val | Glu | His | Leu | Val | Ala |
| | | | | 165 | | | | | 170 | | | | | 175 | |
| Leu | Gly | His | Gln | Gln | Ile | Ala | Leu | Leu | Ala | Gly | Pro | Leu | Ser | Ser | Val |
| | | | 180 | | | | | 185 | | | | | 190 | | |
| Ser | Ala | Arg | Leu | Arg | Leu | Ala | Gly | Trp | His | Lys | Tyr | Leu | Thr | Arg | Asn |
| | | 195 | | | | | 200 | | | | | 205 | | | |
| Gln | Ile | Gln | Pro | Ile | Ala | Glu | Arg | Glu | Gly | Asp | Trp | Ser | Ala | Met | Ser |
| | 210 | | | | | 215 | | | | | 220 | | | | |
| Gly | Phe | Gln | Gln | Thr | Met | Gln | Met | Leu | Asn | Glu | Gly | Ile | Val | Pro | Thr |
| 225 | | | | | 230 | | | | | 235 | | | | | 240 |
| Xaa | Met | Leu | Val | Ala | Asn | Asp | Gln | Met | Ala | Leu | Gly | Ala | Met | Arg | Ala |
| | | | | 245 | | | | | 250 | | | | | 255 | |
| Ile | Thr | Glu | Ser | Gly | Leu | Arg | Val | Xaa | Ala | Asp | Ile | Ser | Val | Val | Gly |
| | | | 260 | | | | | 265 | | | | | 270 | | |
| Tyr | Asp | Asp | Thr | Glu | Asp | Ser | Ser | Cys | Tyr | Ile | Pro | Pro | Ser | Thr | Thr |
| | | 275 | | | | | 280 | | | | | 285 | | | |
| Ile | Lys | Gln | Asp | Phe | Arg | Leu | Leu | Gly | Gln | Thr | Xaa | Val | Asp | Arg | Leu |
| | 290 | | | | | 295 | | | | | 300 | | | | |
| Leu | Gln | Leu | Ser | Gln | Gly | Gln | Ala | Val | Lys | Gly | Asn | Gln | Leu | Leu | Pro |
| 305 | | | | | 310 | | | | | 315 | | | | | 320 |
| Val | Ser | Leu | Val | Lys | Arg | Lys | Thr | Thr | Leu | Ala | Pro | Asn | Thr | Gln | Thr |
| | | | | 325 | | | | | 330 | | | | | 335 | |
| Ala | Ser | Pro | Arg | Ala | Leu | Ala | Asp | Ser | Leu | Met | Gln | Leu | Ala | Arg | Gln |
| | | | 340 | | | | | 345 | | | | | 350 | | |
| Val | Ser | Arg | Leu | Glu | Ser | Gly | Gln | | | | | | | | |
| | | 355 | | | | | 360 | | | | | | | | |